United States Patent [19]

Reithler

[11] Patent Number: 4,653,474
[45] Date of Patent: Mar. 31, 1987

[54] PORTABLE ELECTROMEDICAL DEVICE

[75] Inventor: Jean-Claude Reithler, Wissembourg, France

[73] Assignee: Office de Distribution D'Appareils Medicaux, Wissembourg, France

[21] Appl. No.: 752,506

[22] Filed: Jul. 3, 1985

[30] Foreign Application Priority Data

Jul. 6, 1984 [DE] Fed. Rep. of Germany ....... 3424906

[51] Int. Cl.4 ............................................. A61N 1/02
[52] U.S. Cl. ................................ 128/1 R; 128/419 D; 128/419 R
[58] Field of Search .............. 128/1 R, 419 D, 419 R, 128/630, 709–710; 200/51 R, 51.02, 51.09, 51.1

[56] References Cited

U.S. PATENT DOCUMENTS

| | | | |
|---|---|---|---|
| 3,324,260 | 6/1967 | Schumacher | 200/51 R |
| 3,865,101 | 2/1975 | Saper et al. | 128/419 D |
| 4,097,113 | 6/1978 | McKelvy | 128/419 D |
| 4,116,228 | 9/1978 | Hudspeth et al. | 128/706 |

Primary Examiner—William E. Kamm

[57] ABSTRACT

A portable electromedical device consists of several components, for example a monitor recording unit and a defibrillator. The components are substantially rectangular block-shaped with a forward wall, a rear wall and two sidewalls. In the area of the walls the components are connected together by means of mechanical and electrical plug connections. The sidewalls are provided with lateral shackles in the area bordering the forward wall, which shackles project forwardly beyond the forward wall and at their free ends are connected to one another through a bridging handle. The forward wall and/or the rear wall is provided with a channel running parallel to the handle, and the handle is slidably arranged in the shackles. Upon the connection of two components the free ends of the shackles of one component embrace the sidewalls of the other component, and the handle of the other component is moved into the area of the channels.

12 Claims, 7 Drawing Figures

PORTABLE ELECTROMEDICAL DEVICE

BACKGROUND OF THE INVENTION

The invention concerns a portable electromedical device consisting of several components, for example a monitor-recording unit and a defibrillator, the components being formed at least nearly in the shape of rectangular blocks with each having a forward wall, a rear wall and two sidewalls and which components in the vicinity of their walls are mechanically and electrically connectable by means of plug connections.

One such device is known from manual number 09-10427-07 "LIFEPAK 5" of the firm Physio Control.

The known device consists of several block shaped components which are provided with a rigid handle extending along the entire width of the device at the forward side. The components can be laterally connected with one another through interengaging connectors formed as a slide with a detent. The sidewalls of the components are provided with exposed contacts which upon the connection of the components to one another move into engagement with one another solely for the purpose of transmitting signal voltages and not for transmitting energizing Moreover, the components of the known device consist of—apart from the connecting elements—different housing parts.

Portable electromedical devices are generally used for mobile equipment, especially for emergency equipment. In these applications not only is light weight of the device important but also compact dimensions are also important because such devices must often be carried on board ambulances, emergency medical vehicles, rescue boats and the like or in mobile clinics such as so called "heart alarm vehicles".

Devices of the foregoing type, wherein components can be mechanically and electrically connected with one another, have the advantage that the entire system can be handled with one handle and at the same time all the necessary signal connections can be made, such as, for example, are necessary between a cardiological monitor and a defibrillator in order to synchronize the defibrillator with the heart activity of the patient monitored by the monitor. Moreover, with such a complete unit made of several components the difibrillator electrodes can be used as EKG electrodes and the EKG signal can be displayed on a screen of the monitor or for example can be used to indicate the pulse frequency. Also, with corresponding combinations of the unit the EKG signal can also be documented by means of a recorder.

On the other hand this apparatus also has the advantage that the components can be used separately and individually, for example when part of an emergency medical equipment in the case of a traffic accident the device can be separated into its components and the individual components can be used for different accident victims.

The previously mentioned known device does not serve all requirements which can be set for such devices. One objection pertains to the requirement for minimal dimensions insofar as in the known device in the connected condition of the parts both of the handles of the components project outwardly and require space, although a single handle is sufficient. Moreover, the freely exposed contacts for the signal voltages have a disadvantage that electrical disturbances from outside the device can be picked up and can lead for example to erroneous synchronization or false signals. Moreover, the known device has the disadvantage that because of the absence of the possibility of transmitting a source of current from one component to the other component a fully functional current source must be provided in each component and for example in the case of a drained battery of one component the other component cannot be used as a current source and/or to recharge the drained battery. Finally, in the known device there is also the disadvantage that because of the differences in the components the manufacturing as well as the warehousing by suppliers is very complicated and expensive.

The invention therefore has as its object an improvement in a device of the aforedescribed type which in a minimum amount of space for the components which are assembled with one another assures the highest degree of electrical safety and which is as well improved with respect to the avoidance of the pickup of disturbing voltages as well as improved with respect to the current supply and which is simplified as to its manufacture and maintenance and which is therefore more economical.

These objects are met by the invention in that the sidewalls of each component in the areas which border on the forward wall are provided with lateral shackles which project forwardly beyond the forward wall and at their free ends are connected by a handle extending between them, in that the forward wall and/or the rear wall is provided with a channel extending parallel to the handle and in that the handle is slidably connected with the shackles so that upon the connection of two components the free ends of the shackles of one component embrace the sidewalls of the other component and the handle becomes positioned in the vicinity of the channel.

The device of the invention has the essential advantage that a complete device assembled from components only has one handle on its forward side by means of which the device can be taken from a holder or shelf and carried. The handles of the other components in this case are pushed into the channels and require no additional space. If the components are again separated from one another each component again has its own handle and can be handled by itself.

According to a further refinement of the invention the handle upon the connection of two components can be guided against the force of a spring.

This measure has the advantage that upon the separation of two connected components the retracted handle of the one component moves outwardly by itself under the force of the spring and can immediately be grasped.

Advantageously the grip in a device of the invention moves relative to the shackles by means of pins arranged on its ends which move in guide grooves in the shackles.

In a further embodiment of the invention the shackles are provided with mechanical and/or electrical connecting means which cooperate with mechanical and/or electrical connecting means arranged on the area of the rear wall bordering the sidewalls of another component.

This measure has the advantage that one or more of the electrical and/or mechanical connecting means are arranged on the inner side of the shackles and therefore are practically not accessible from the outside. An inadvertent short-circuiting of the connecting means by lateral movement of an electrical conducting object is therefore avoided.

In a preferred embodiment the mechanical connecting means are made of at least one resilient detent in one component which detent cooperates with a recess in the other component.

This arrangement guarantees an especially secure mechanical connection with at the same time an uncomplicated and disturbance-proof construction.

The last-named embodiment is preferably further formed with the detents arranged in the shackles so that the detents are movable, by means of an operating knob, in a guide inclined to the direction in which the components are moved into connection with one another against the force of a spring out of engagement with the recesses.

This measure has as one advantage that the mechanical connection is especially easily made and secure because the detents work in the area in which the shackles laterally embrace the other components.

Moreover the mentioned features have the advantage that the mechanical detent connection is easily released by a simple actuation of the knobs, a property which is of especial significance in the case of emergency devices.

In a further preferred embodiment of the invention the electrical connecting means are formed as contact springs in a component which contact springs cooperate with contact pins or contact strips in another component.

This measure has the advantage that through suitable adjustment of the contact pressure of the springs the contact fork can be definitely guaranteed upon the pushing together of the components and when the components are in their connected state. Moreover, the contact pins and contact strips have the advantage that they fixedly project outwardly from the upper surface of the device so that dirt and other deposits are not to be feared.

In an especially preferred form of the invention a switch is arranged in the area of the shackle which is operated upon the connection of two components, the contacts of which switch are in series with the electrical connecting means.

This feature has the essential advantage that for example the electrical connecting means on which appear signal or supply voltages can be made nonconducting in the event of nonconnected components and those electric connecting means which serve as input means are separated from the remaining electrical units of the components. Therefore, neither signal nor supply outputs can be short-circuited nor signal inputs be effected by disturbing voltages because the electrical connecting means are only switched to one another when the components are connected with one another.

Preferably the latter switch is provided in the form of a microswitch whose operating member is arranged to be operated by the contact spring.

This has the advantage that an especially small number of components are required because the placement of the contact spring serves simultaneously to actuate the microswitch.

In another embodiment of the invention the switch can also be provided by a microswitch, in which embodiment the actuating member of the microswitch is operated upon the bringing together of the shackles of one component with bonnets on another component, which bonnets upon connection of the components border the shackles.

This embodiment is especially suited to that situation in which a large microswitch must be used whose actuating force and/or actuating movement is larger than in the case of the aforementioned embodiment.

In another form of the invention the electrical connecting means of one lateral latch serve to transmit physiological signals and the connecting means of the other lateral latch serve to transmit supply currents.

This measure has the advantage that despite the use of similar contact elements an exchange of the connections cannot be made.

Finally in a further form of the invention the components each consist of an individualist upper portion and a middle portion and a lower portion which middle and lower portions are similar from one component to another and wherein the middle portion has arranged on it the shackles and the channel.

This measure has the advantage that the manufacture and maintenance of the devices is considerably simplified because with the exception of the upper portion, which must be different from one component to the other because of the differing functions of the devices, identical parts can be used. Furthermore, this meausre also has the advantage that different components can be placed in similar holders or partitions of ambulances, helicopters or the like because the breadth and depth of the parts are the same.

Further advantages will be apparent from the following description and the accompanying drawings.

Embodiments of the invention are illustrated in the drawings and are explained in more detail below. The drawings are:

DETAILED DESCRIPTION OF THE PREFERRED EMBODIMENT

Figure 1:
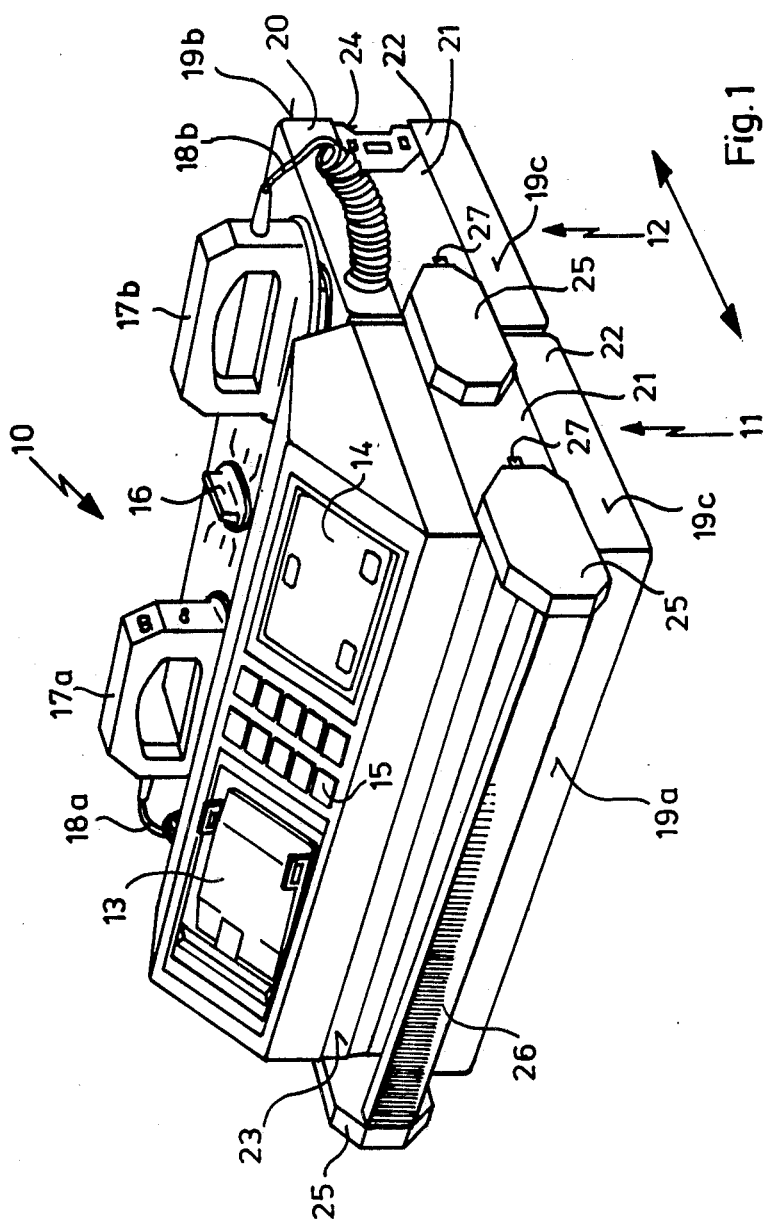
FIG. 1 is a perspective view taken obliquely from above of a device comprising one embodiment of the invention.

In FIG. 1 reference numeral 10 indicates generally a portable electromedical device comprising one embodiment of the invention. This embodiment according to FIG. 1 is comprised of two components, namely a monitor-recorder unit 11 and a defibrillator 12. The unit 11 has a recorder 13 in its upper left hand corner and has a monitor-indicator unit 14 in its upper right hand corner. Between these two units is a set of function keys 15. The recorder 13 and the monitor-indicator unit 14 can be controlled by the function keys 15, for example to record an EKG signal, to display the EKG signal on a picture tube of the monitor or to indicate the value of the heart beat frequency or to set a lower and a upper limit for the heart beat frequency, to distinguish slow and fast hearts and to enable the production of a signal indicating the same.

The defibrillator 12 is put into play through an adjustment switch 16 by means of which the energy delivered by the difibrillator can be preselected. Two electrodes 17a and 17b are set onto the upper side of the defibrillator 12 and are connected with the difibrillator through flexible spiral cables 18a, 18b.

It will be understood that the combination shown in FIG. 1 comprising a device 10 represents only one example of the invention. Within the bounds of the present invention it will be evident that other combinations of electromedical devices can be combined with one another, including pacemakers, breath frequency monitors, temperature monitors and the like.

It will also be seen from FIG. 1 that each of the two components consist of an upper portion 20, a middle portion 21 and a lower portion 22. The upper portion 20 of each component is individualistically formed—the upper portion 20 of the monitor-recording unit 11 containing the already mentioned components 13 to 15, whereas the upper portion 20 of the defibrillator 20 is essentially formed for receiving the electrodes 17a, 17b.

The middle portions 21 and the lower portions 22 of both components are formed entirely identically, and this can also be true for the interior construction of these portions so that, for example, the lower portions 22 are provided with similarly constructed circuit devices and the middle portions 21 are provided at least with similarly constructed holders for different types of electronic circuit boards.

The components illustrated in FIG. 1 each include a forward wall 19a, a rear wall 19b and sidewalls 19c. In the area of the forward wall 19a and of the rear wall 19b each middle portion 21 is provided with either a forward channel 23 or a rear channel 24. The channels 23, 24 have a nearly trapezoidly shaped cross-section.

Further, shackles 25 are mounted on the sidewalls 19c of the middle portions 21 at the area bordering the forward walls 19a. In the illustrated embodiment the clear distance between the free ends of the shackles 25 is as large as the width of the forward wall 19a. It will however be understood that it is also possible to provide the sidewalls 19c in the area bordering the rear wall 19b with lateral recesses partially or entirely receiving the shackles so that the clear distance between the free ends of the shackles 25 can be smaller than the width of the forward wall 19a, leading generally to a sidewall 19c free of projections.

In the embodiment of FIG. 1 a handle 26 is arranged between the free ends of the shackles 25 by means of which handle the device 10 can be taken hold of and carried. Moreover, knobs 27 are provided on the opposite ends of the shackles 25 which serve to release the connection between the components as is described hereinafter in more detail in connection with FIG. 5.

In any event, as explained in more detail, below the shackles 25 are provided on their free inner sides with electrical and mechanical connection means which cooperate with corresponding connection means arranged on the middle portion 21 of the sidewalls at the areas bordering the rear wall 19b. For connecting two components, for example the monitor-recording unit 11 and the defibrillator 12 of FIG. 1, these components are arranged next to one another and are pushed together in the direction of the arrow shown directly under FIG. 1. As further indicated below, the handle 26 of the defibrillator 12 thereby retracts into the intermediate space formed by the adjacent channels 23, 26.

If the components are thereafter to be separated, it is only necessary to press one or two of the knobs 27 and to pull the two components apart in the direction of the arrow.

When the two components are in connected condition all necessary signal connections are made and the current supplies are so coupled with one another through the electrical connecting means, so that the entire device can be driven from the current supply of one individual one of the components, but if the connections are broken by separating the components each component is capable of functioning by itself.

Figure 2:
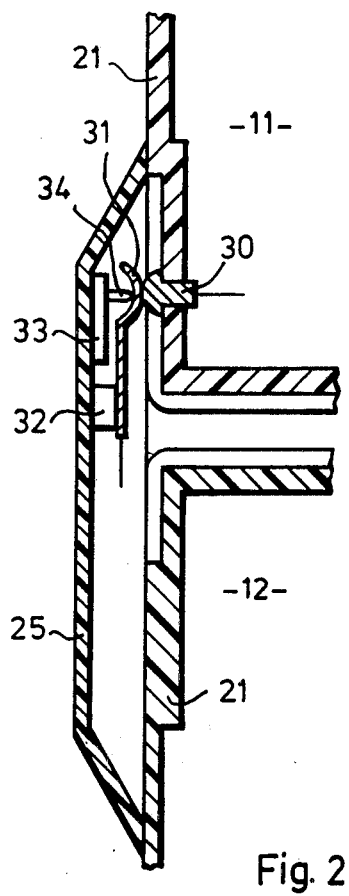
FIGS. 2 and 3 are cross-sectional views taken in two different planes of one form of electrical connecting means and one form of mechanical connecting means which can be used with a device embodying the invention.
Figure 3:
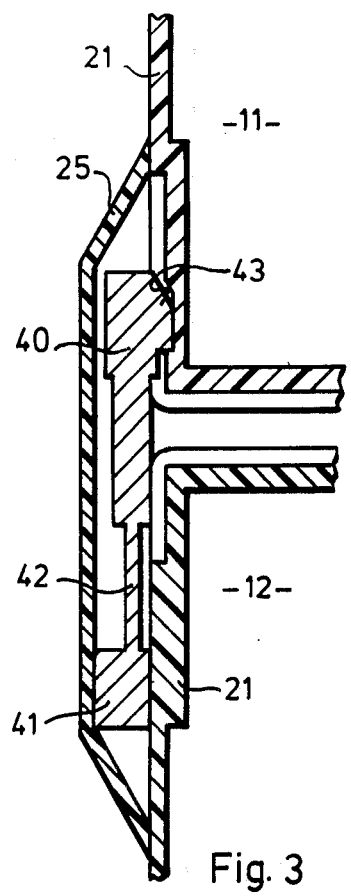

FIGS. 2 and 3 illustrate one embodiment of electrical and mechanical connecting means which can be used in the device of FIG. 1. The sectional illustration of FIG. 2 shows one shackle 25 in a sectional plane somewhat below or above the longitudinal middle plane of the shackle, whereas the illustration of FIG. 2 goes generally through the middle plane of the shackle.

From FIG. 2 it will be seen that a contact pin 30 is embedded in the middle part 21 of the monitor-recording unit 11 which cooperates with a resilient contact spring 31 when connected with a defibrillator 12, which spring is fastened to a pedestal 32 fastened to the inside of the shackle 25. Upon the pushing together of the components the contact spring 31 moves onto the head of the contact pin 30 and is bent slightly toward the left as seen in FIG. 2. For detection of a complete connection a microswitch 33 is also carried by the inner side of the shackle 25, the operating member 34 of which engages the contact spring 31. When the contact spring 31 is moved to the left, as in FIG. 2, the microswitch 33 is actuated.

It will be understood that the type of connecting means shown in FIG. 2 can be provided in larger number to deal with as many signal and current connections as may be necessary.

FIG. 3 shows the mechanical connecting means of the illustrated embodiment in the form of a detent 40 fastened on a pedestal 41 in the shackle 25. Between the pedestal 41 and the detent 40 is a reduced section portion 42 so that the detent 40 can be resiliently deflected toward the left in the plane of the drawing of FIG. 3. If the defibrillator 12 is now connected, as seen in FIG. 3, with the monitor-recorder unit 11, the detent 40 will first deflect to the left and then snap into a recess 43 in the middle part 21 of the monitor-recorder unit 11. The means for releasing the detent connection are not shown in FIG. 3 and are explained in more detail below in connection with FIG. 5.

Figure 4:
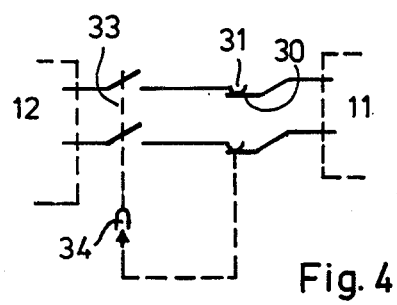
FIG. 4 is a schematic view of a current circuit for explaining the operation of the electrical connecting means.

FIG. 4 shows schematically a simple current path for the electrical connection between the defibrillator 12 and the monitor-recorder unit 11. It is seen that the contact of the microswitch 33 is in series with the electrical connecting means, namely the contacts formed by the contact pin 30 and the contact pin 31. The broken lines indicate the actuating member 34 whereby the microswitch 33 is actuated in the described way by the contact spring 31. When the contacts of the microswitch 33 are open the contact springs 31 serving for example as signal inputs are electrically disconnected so that no disturbing radiation can enter the defibrillator 12 and there, for example, lead to an unsynchronized application of the electroshock. It will be understood, that, although not shown in FIG. 4, corresponding microswitches can also be provided on the side of the monitor-recording unit 11.

Figure 5:
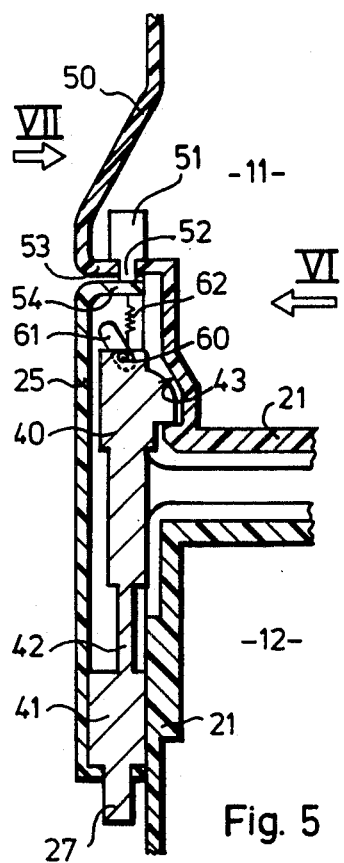
FIG. 5 is a view similar to that of FIG. 3 but illustrating a further embodiment of the invention.

FIG. 5 shows a variation from the means shown in FIG. 3 in which variation the middle portion 21 of the monitor-recording unit 11 is provided with a bonnet 50 which in the connected condition of the components borders a forward wall 54 of the shackle 25 by means of an oppositely disposed forward wall 53. In the forward wall 53 of the bonnet 50 is an opening for a switch actuating member 52 of a microswitch 51. Upon the pushing together and therewith the connection of the two components the forward wall 54 of the shackle 25 thereupon presses on the actuating member 52 and through it actuates the mircroswitch 51 so that it is switched as represented in FIG. 4 for the microswitch 33.

It will further be seen from FIG. 5 that the resilient detent 40 is provided laterally with a pin 60 which moves in a guide groove 61 inclined relative to the direction in which the connection is made. Moreover, a pressure spring 62 is arranged between the detent 40 and the forward wall 54. The pedestal 41 which carries the detent 40 terminates in a knob 27 which extends away from the end opposite the detent 40.

If one wants to disconnect the monitor-recording unit 11 from the difibrillator, this can be done by pressing the knob 27 in FIG. 5 upwardly against the force of the pressure spring 62. The detent 40 is thereby, through the inclined guide groove 61 and the pin 60, guided upwardly toward the left so that it moves out of engagement with the recess 43 and thereupon the defibrillator 12 can be moved away from the monitor-recorder unit 11, after which when the knob 27 is released the pressure spring 62 serves to return the detent 40 again into its original position toward the right at which it is ready when necessary to receive another component when the next connection is made.

Figure 6:
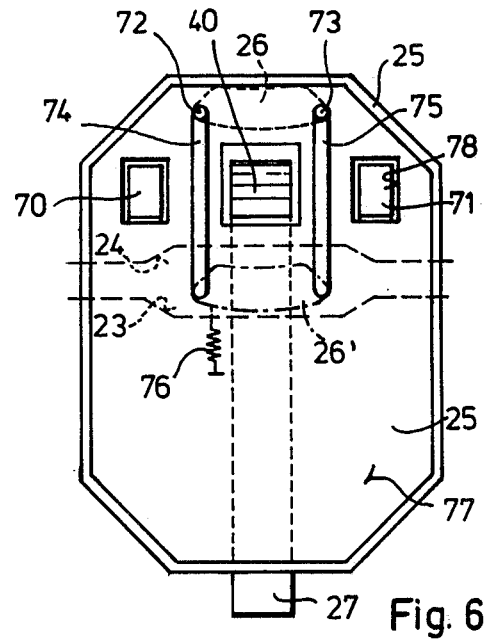
FIGS. 6 and 7 are views of a shackle and a bonnet taken respectively in the direction of the arrows VI and VII of FIG. 5.

FIG. 6 shows a view of the shackle 25 taken in the direction of the arrow, VI of FIG. 5. It will first of all be seen that two contacts 70, 70 are arranged laterally from the middle and can, for example, be made similar to the contact spring 31 of FIG. 2. It is further seen that at the upper edge of the shackle 25 is the handle 26, shown by the broken lines, in the position taken by the handle 26 of the monitor recording unit 11 of FIG. 1. The handle 26 is provided laterally with pins 72, 73 which move respectively in a guide groove 74 or a guide groove 75 of the shackle 25 in a direction corresponding to the direction along which two components are moved together in making a connection. The handle 26 in this case moves downwardly, slides over the resilient detent 40 and finally achieves a lower position indicated by the reference number 26' in the FIG. 6 wherein it lies inside of the space bounded by the channels 23, 24. The handle 26 in this case moves against the force of a pressure spring 76, shown only schematically in FIG. 6, so that when the components are again separated from one another the handle 26 will return by itself to the upper basic position shown in FIG. 6.

The shackle 25 can be provided on its inwardly turned side with a cover 77 in which the guide grooves 74, 75 are provided. Moveover, windows 78 are provided in the cover 77 for the contacts 70, 70 and for the detent 40, so that all of the elements contained in the shackle 25 have an optimum amount of protection.

Figure 7:
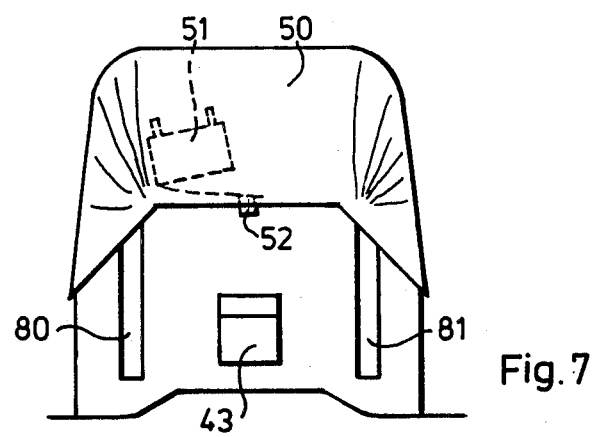

FIG. 7 shows finally a view of the bonnet 50 in the direction of the arrow VII of FIG. 5.

It will first of all be seen that the microswitch 51 with its actuating member 52 is contained in the part covered by the bonnet 50. Below the bonnet 50 is the recess 43 for the detent 40 and laterally therefrom are contact strips 80, 81 which cooperate with the contacts 70, 71 of FIG. 6. It will, of course, be understood that instead of the contact strips 80, 81 contact pins 30 of the kind shown in FIG. 2 can also be used.

Instead of the spring contacts 70, 71/80, 81 plug type contacts can also be used. In connection with this, the shackle 25 can be so formed at its upper end that in the connected condition of two components it extends to or under or over the bonnet 50 or its forward wall 53 with the shackle 25 having plug contacts on its forward wall 53 or on the adjacent forward wall 54 which correspond to that shown for the microswitch 51 in FIG. 5.

I claim:

1. A portable electromedical device, said device comprising at least two components, said components being substantially rectangular block-shaped with each having a forward wall, a rear connecting wall, and two sidewalls, and said components having means in the area of said walls for mechanically and electrically releasably connecting said components to one another, said connecting means including a pair of lateral shackles on each component connected to said sidewalls of that component in the area bordering the forward wall, which shackles project forwardly beyond the forward wall, a handle extending between the free ends of said shackles, and at least one of said forward wall and rear wall of each component being provided with a channel running parallel to its said handle, and means slidably connecting each handle to its shackles so that upon the connection of two components the free ends of the shackles of one component embrace the sidewalls of the other component and the handle connected to said embracing shackles is moved into the area of one of said channels.

2. A device according to claim 1 further characterized in that said means for connecting each handle to its shackles being such taht said handle is movable between a normal and a retracted position relative to said shackles, and a spring means biasing said handle to said normal position.

3. A device according to claim 1 further characterized in that said means for connecting each handle to its shackles includes guide grooves in said shackles and pins provided on the ends of said handle and slidable in said grooves.

4. A device according to claim 1 further characterized in that said shackles of one component are provided with mechanical and electrical connecting members which cooperate with mechanical and electrical connecting members provided on the area of the sidewalls of another component in the area of its rear wall.

5. A device according to claim 4 further characterized in that a switch is arranged in the area of the shackles which is actuated upon the connection of two components, the contacts of which switch are connected in series with said electrical connecting members.

6. A device according to claim 5 further characterized in that said switch is formed as a microswitch whose actuating member is arranged to be operated by one of said electrical connecting members.

7. A device according to claim 5 further characterized in said the switch is formed as a microswitch whose actuating member is operated upon the bringing together of the shackles of one component with a bonnet on another component, which bonnet borders a shackle when said components are in their connected condition.

8. A device according to claim 4 further characterized in that the electrical connecting members of one lateral shackle serve to transmit physiological signals and the electrical connecting members of the other lateral shackle serve to transmit supply currents.

9. A device according to claim 1 further characterized in that said connecting means includes at least one resilient detent on one component which cooperates with a recess in another component.

10. A device according to claim 9 further characterized in that said detent is arranged in a shackle, said detent being movable in a guide inclined to the direction in which said components are moved into connection with one another with such movement of said detent being accomplished by means of a knob against the force of a spring to bring it out of cooperation with said recess.

11. A device according to claim 1 further characterized in that said connecting means includes a contact spring in one component which contact spring cooperates with a contact pin in another component.

12. A device according to claim 1 further characterized in that said components are each formed of an individualistic upper portion and of a middle portion and a lower portion which middle portions and lower portions are similar from component to component, and in that said shackles as well as said channels are arranged on said middle portions.

* * * * *